(12) United States Patent
Weilbacher

(10) Patent No.: US 7,981,089 B2
(45) Date of Patent: Jul. 19, 2011

(54) VIAL ACCESS DEVICE

(75) Inventor: Eugene E. Weilbacher, Chesterfield, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/409,098

(22) Filed: Mar. 23, 2009

(65) Prior Publication Data

US 2009/0247962 A1  Oct. 1, 2009

Related U.S. Application Data

(60) Provisional application No. 61/041,030, filed on Mar. 31, 2008.

(51) Int. Cl.
*A61M 5/31* (2006.01)

(52) U.S. Cl. .......................... 604/243; 604/414

(58) Field of Classification Search ................ 604/239, 604/240, 411
See application file for complete search history.

(56) References Cited

U.S. PATENT DOCUMENTS

| | | | |
|---|---|---|---|
| 2,541,272 A | 2/1951 | Murphy | |
| 2,752,919 A | 7/1956 | Gabriel | |
| 4,387,879 A | 6/1983 | Tauschinski | |
| 4,675,020 A | 6/1987 | McPhee | |
| 4,710,180 A | 12/1987 | Johnson | |
| 4,723,955 A | 2/1988 | Vaillancourt | |
| 4,842,591 A | 6/1989 | Luther | |
| 5,059,172 A | 10/1991 | Sutherland et al. | |
| 5,167,642 A | 12/1992 | Fowles | |
| 5,188,620 A | 2/1993 | Jepson et al. | |
| 5,211,638 A | 5/1993 | Dudar et al. | |
| 5,411,499 A * | 5/1995 | Dudar et al. | 604/411 |
| 5,470,327 A | 11/1995 | Helgren et al. | |
| 5,584,819 A * | 12/1996 | Kopfer | 604/239 |
| 5,746,733 A | 5/1998 | Capaccio et al. | |
| 5,755,696 A | 5/1998 | Caizza | |
| 5,820,621 A | 10/1998 | Yale et al. | |
| 5,832,971 A | 11/1998 | Yale et al. | |
| 5,833,674 A | 11/1998 | Turnbull et al. | |
| 5,887,633 A | 3/1999 | Yale et al. | |
| 5,919,182 A | 7/1999 | Avallone | |
| 5,928,162 A | 7/1999 | Giurtino et al. | |
| 5,928,215 A | 7/1999 | Caizza et al. | |
| 5,976,115 A | 11/1999 | Parris et al. | |
| 6,206,858 B1 | 3/2001 | Kempen et al. | |
| 6,358,236 B1 | 3/2002 | DeFoggi et al. | |
| 6,394,979 B1 | 5/2002 | Sharp et al. | |
| 6,585,697 B2 | 7/2003 | Kempen et al. | |
| 6,637,470 B2 | 10/2003 | Reihl et al. | |
| 6,715,520 B2 | 4/2004 | Andreasson et al. | |
| 6,832,994 B2 | 12/2004 | Niedospial, Jr. et al. | |

(Continued)

*Primary Examiner* — Theodore J Stigell
*Assistant Examiner* — Brandy C Scott
(74) *Attorney, Agent, or Firm* — Lisa E. Winsor, Esq.

(57) ABSTRACT

A needle assembly is disclosed, which includes a needle hub, a metal cannula and a plastic tip. The needle hub defines a fluid flow path therethrough. The metal cannula is supported on a distal end of the needle hub, where the metal cannula defines a fluid flow path into the distal end of the needle hub. The plastic tip member is connected to a distal end of the metal cannula, where the plastic tip member defines a fluid flow path into the distal end of the metal cannula. Plastic tip further includes a channel groove that runs along the length of the plastic tip to allow fluid to flow into a distal end of the metal cannula. Additionally, the plastic tip member is configured to pierce a septum of a vial.

16 Claims, 4 Drawing Sheets

U.S. PATENT DOCUMENTS

| | | |
|---|---|---|
| 6,875,205 B2 | 4/2005 | Leinsing |
| 6,921,395 B2 | 7/2005 | Carano et al. |
| 2002/0019622 A1 | 2/2002 | Daubert et al. |
| 2004/0024354 A1 | 2/2004 | Reynolds |

* cited by examiner

VIAL ACCESS DEVICE

CROSS REFERENCE TO RELATED APPLICATION

This patent application claims priority to U.S. Provisional Application Ser. No. 61/041,030, filed Mar. 31, 2008, which is incorporated herein in its entirety by reference.

BACKGROUND

1. Technical Field

The present disclosure relates to needle assemblies and, more particularly, to needle assemblies for accessing a stopper vial without the need for inverting the vial.

2. Description of Related Art

In the medical field, fluid transfer devices, particularly, vial access devices are commonly used to draw medicaments from medical vials in order to fill syringes. Medical vials are well known in the medical field and typically include a pierceable septum and a medicinal fluid. Vial access devices typically include a syringe having a syringe body, a plunger assembly, and a needle or cannula hub assembly. Typically, the needle assembly includes a needle or cannula configured to pierce a septum of a vial and a needle hub which can be removably attached to the syringe body. The needle or cannula can be formed from metal or plastic. After medical fluid has been withdrawn from a medical vial into the syringe, the needle hub assembly can be removed from the syringe body, such that, an intravenous catheter or a syringe needle may be connected to the filled syringe to deliver the medicament into a patient.

There are certain medicaments, which are stored in vials, that should not be physically disturbed, e.g., by inverting the vial to access the medicament that remains in the bottom portion of the vial. Current medical practice requires the use of a relatively long cannula assembly, e.g., about 1.5 inches, to access the bottom portion of such a vial. Although, plastic needles are desirable because they present less of a risk of needle-stick injury, plastic needles are weaker than metal needles and generally can be no longer than about ½ inch in length before their diameters become unreasonably large. Thus, plastic needles cannot be used to access such vials because of their weakness.

Accordingly, a continuing need exists in the medical arts for a fluid transfer device which can access vials greater than ½ inch in depth, while at the same time being less likely to cause needle stick injuries.

SUMMARY

A needle assembly is disclosed, which includes a needle hub, a metal cannula and a plastic tip. The needle hub defines a fluid flow path therethrough. The metal cannula is supported on a distal end of the needle hub and defines a fluid flow path into the distal end of the needle hub. The plastic tip is connected to a distal end of the metal cannula and defines a fluid flow path into the distal end of the metal cannula. The plastic tip further includes a channel groove that runs along at least a portion of the length of the plastic tip to allow fluid to flow into a distal end of the metal cannula. Additionally, the plastic tip is configured to pierce a septum of a vial.

In embodiments, the needle assembly is adapted to connect to a syringe assembly which includes a plunger assembly and a syringe body. The syringe assembly is operably and fluidly connected to the needle hub. The syringe body defines a fluid reservoir and a fluid outlet. The plunger assembly includes a plunger rod and a plunger head which is configured to be slidably received within the fluid reservoir of the syringe body.

The needle hub includes a tubular body portion that defines a fluid flow path fluidly connected to the metal cannula, a grip portion, and a first coupling member. The first coupling member is configured to engage a second coupling member of the syringe assembly to releasably secure the needle hub to the syringe assembly.

In embodiments, the first coupling member defines a female luer-type connector and has a plurality of tabs configured to rotatably engage threads of the second coupling member of the syringe assembly. The second coupling member defines a male luer-type connector.

The plastic tip includes a piercing distal end having an arrow-shaped point which is configured to pierce a penetrable surface of a septum and a central segment in fluid communication with a proximal end of the plastic tip. The plastic tip includes a flanged portion which is operably positioned to engage the distal end of the metal cannula. The plastic tip is coupled to the distal end of the metal cannula by a suitable fastening technique (e.g., gluing, snap-fitting, crimping, press-fitting, and molding).

The channel groove of the plastic tip extends partially within the distal end of metal cannula and defines a continuous flow path to the metal cannula.

In embodiments, the distal end of metal cannula includes a first diameter portion and a second diameter portion. The first diameter portion tapers outwardly to the second diameter portion, where the second diameter portion is greater in diameter than the first diameter portion. The second diameter portion is dimensioned to receive a proximal end of the plastic tip. The plastic tip includes a distal end, a central portion, and a proximal end. The central portion has the same diameter as the second diameter portion of the metal cannula and is operably connected to the second diameter portion of the metal cannula. The proximal end is configured to taper to a smaller diameter and have a substantially similar diameter to the first diameter portion of the metal cannula.

BRIEF DESCRIPTION OF THE DRAWINGS

Various embodiments of the presently disclosed medical vial access device are disclosed herein with reference to the drawings, wherein.

DETAILED DESCRIPTION

Figure 1:
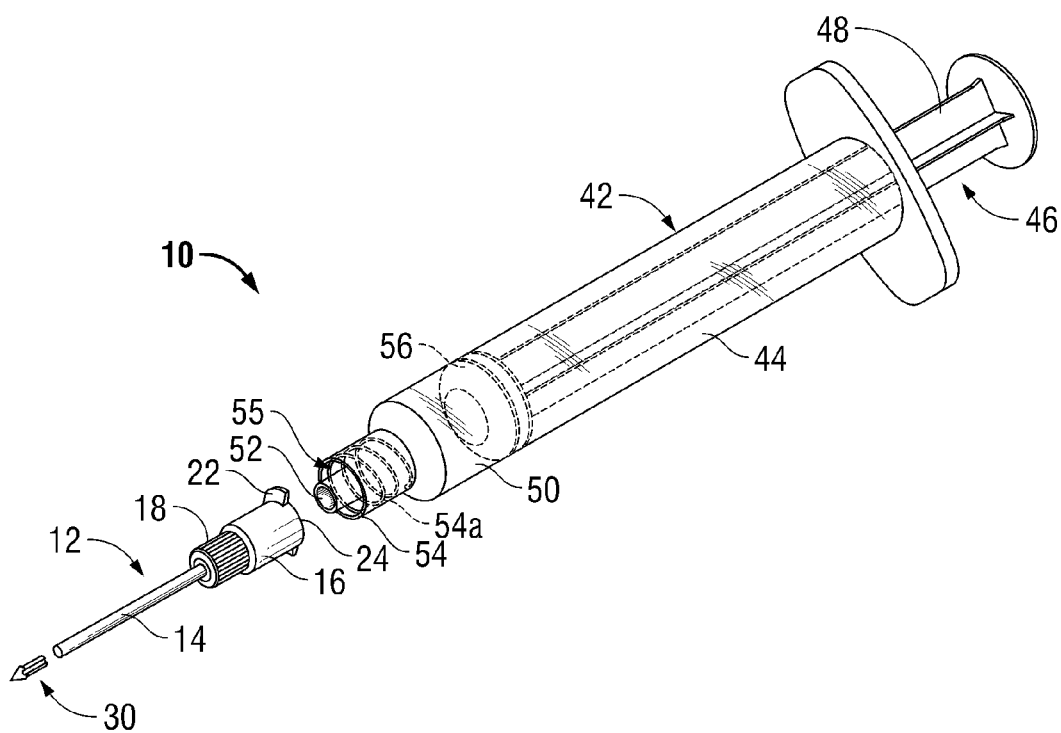
FIG. 1 is a partially exploded perspective view of one embodiment of the presently disclosed vial access device having a plastic tip and a syringe assembly.
Figure 2:
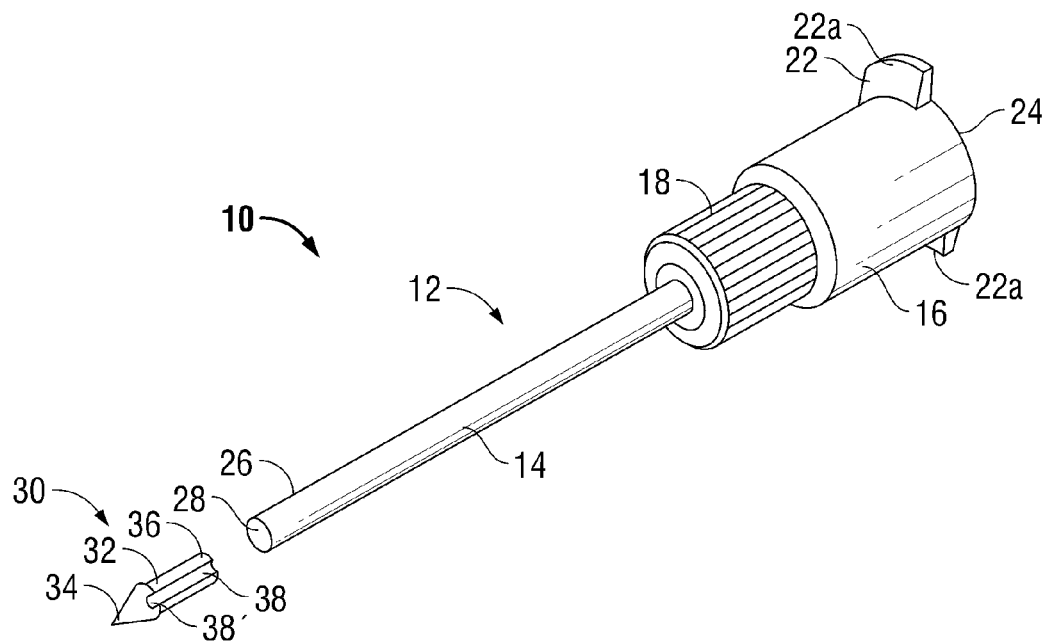
FIG. 2 is an exploded perspective view of the needle hub and the plastic tip of the vial access device shown in FIG. 1.

Embodiments of the presently disclosed vial access device will now be described in detail with reference to the drawings wherein like reference numerals designate identical or corresponding elements in each of the several views. In this description, the term proximal is generally used to indicate the relative nearness of a referenced item to a user of a device and the term distal is used to indicate the relative remoteness of a referenced item to a user of the device.

Referring initially to FIG. 1, a vial access device 10 is provided, which generally includes a syringe assembly 42, a needle hub assembly 12, and a plastic tip 30. The syringe assembly 42 includes a plunger assembly 46 and syringe body 44, that is connected in fluid communication with the needle hub assembly 12. The needle hub assembly 12 includes an elongated metal cannula 14, which is connected to a distal end of a hub body portion 16 of hub assembly 12. A plastic tip 30 is connected to a distal end of metal cannula 14. Plastic tip 30 includes channel grooves 38a-c (shown in FIG. 3C), that define a flow path into the distal end of the metal cannula 14. All of the above-mentioned components will be discussed in greater detail below.

As discussed above, syringe assembly 42 includes a syringe body 44 and a plunger assembly 46. Body 44 defines a fluid reservoir 50. Plunger assembly 46 includes a plunger rod 48 and a plunger head 56. Plunger head 56 is configured to be slidably received within reservoir 50 of syringe body 44 to deliver fluid from reservoir 50 to a fluid outlet 52, which is supported on a distal end of body 44 in fluid communication with reservoir 50. Syringe assembly 42 also includes an annular coupling member 54 positioned partially about fluid outlet 52 as will discussed in further detail below.

Hub assembly 12 can be formed from a metal or plastic material, e.g., polyethylene, and includes body portion 16, a grip portion 18, a coupling member 22, and elongated metal cannula 14. The body portion 16 of hub assembly 12 is tubular and defines a fluid channel 24 therein and is connected in fluid communication with metal cannula 14. The metal cannula 14 defines a fluid flow path having an outlet 28 to allow fluid to pass through. The grip portion 18 of the hub assembly 12 allows a user to firmly grip the hub assembly 12 when engaging or disengaging hub assembly 12 from the coupling member 54 of syringe assembly 42, as will be discussed in further detail below.

Coupling member 22 is configured to releasably engage annular coupling member 54 of syringe 42 to releasably secure hub assembly 12 to syringe assembly 42. As illustrated, coupling member 22 may be a female luer-type coupling member which includes tabs 22a configured to rotatably engage threads 54a of annular coupling member 54 which is configured as a male luer-type coupling member. It is envisioned that a variety of different types of coupling members, for example, bayonet-type, snap-fit type or any other suitable coupling members could be used to couple hub assembly 12 to syringe assembly 42.

In order to attach the hub assembly 12 to the syringe assembly 42, coupling member 22 is inserted into an annular recess 55 defined between the annular coupling member 54 and fluid outlet 52 and rotated in relation to syringe assembly 42 in a first direction (clockwise) such that tabs 22a of coupling member 22 engage and interlock with threads 54a of annular coupling member 54. Hub assembly 12 can be detached from syringe assembly 42 by rotating the hub assembly 12 in a second direction (counter-clockwise direction) in relation to syringe assembly 42.

Figure 3A:
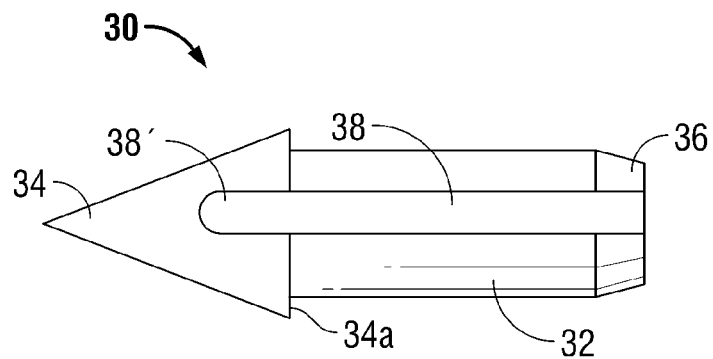
FIG. 3A is a side view of the plastic tip of the vial access device shown in FIG. 1.
Figure 3B:
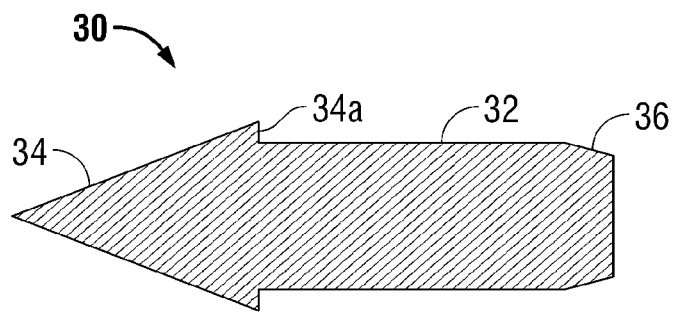
FIG. 3B is a side cross-section view of the plastic tip of the blood collection device shown in FIG. 1.
Figure 3C:
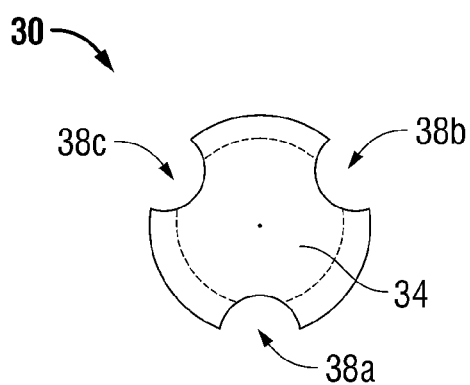
FIG. 3C is a top view of the plastic tip of the vial access device shown in FIG. 1.
Figure 4A:
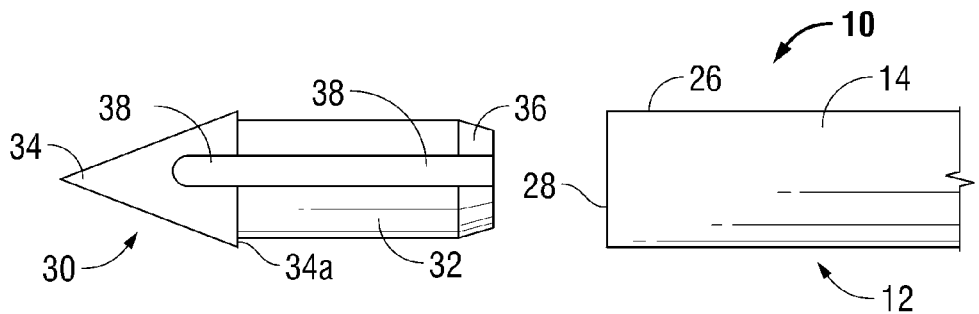
FIG. 4A is a partial exploded side view of the plastic tip and the distal end of the needle hub assembly of the vial access device shown in FIG. 1.
Figure 4B:
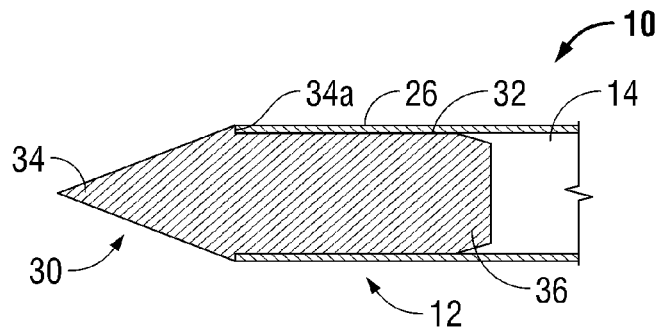
FIG. 4B is a side cross-section view of the plastic tip of the vial access device being inserted into the needle hub assembly shown in FIG. 4A.

As shown in FIGS. 3A-3C, the plastic insert tip 30 includes a piercing distal end 34, a central segment 32 and a proximal end 36. The distal end 34 may be dimensioned to have an arrow-shaped point and configured to pierce a penetrable surface (e.g., pierceable septum, membrane, etc.). The distal end 34 also includes a flanged portion 34a, so that the flanged portion 34a abuts the blunt distal end 26 of the metal cannula 14, thus keeping the plastic tip 30 securely attached to the metal cannula 14, as shown in FIGS. 4A and 4B. In alternative embodiments, the plastic tip member 30 may be formed from a thermoformable material, and the shape of the distal piercing surface may be achieved by a manufacturing process, for example, injection molding, overmolding, or using a mold.

The plastic tip 30 may be attached to the blunt distal end 26 of metal cannula 14 by glue, snap-fit, crimping, press-fit, molding, or by using any other suitable connecting technique.

The channel groove 38 of plastic tip 30 comprises an external portion 38' and internal portion 38, which runs along the length of the plastic tip. The external channel groove 38' is positioned distally of metal cannula 14, as shown in FIG. 4B. Channel grooves 38' and 38 create a continuous flow path from within metal cannula 14 through outlet 28 at distal end 26 of metal cannula 14 to allow medicinal fluid or any type of fluid to flow into the reservoir 50 of syringe 42. The plastic tip 30 may have more than one channel grooves, as shown in FIG. 3C.

Figure 5A:
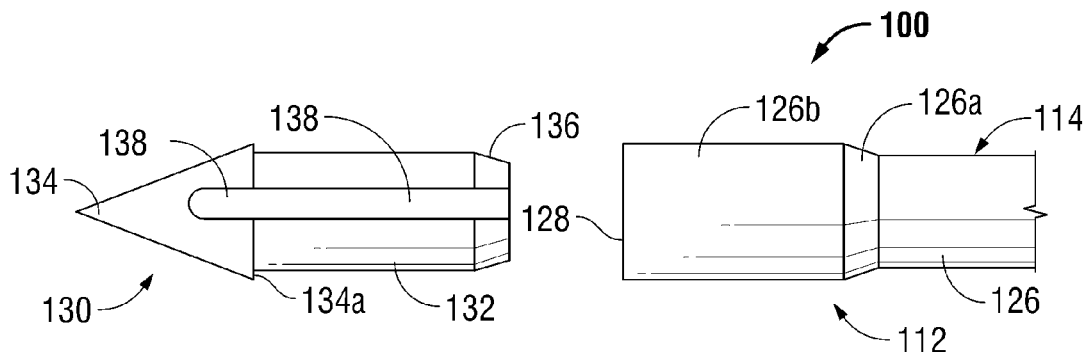
FIG. 5A is a partial exploded side view of another embodiment of a plastic tip and a needle hub assembly of the presently disclosed vial access device.
Figure 5B:
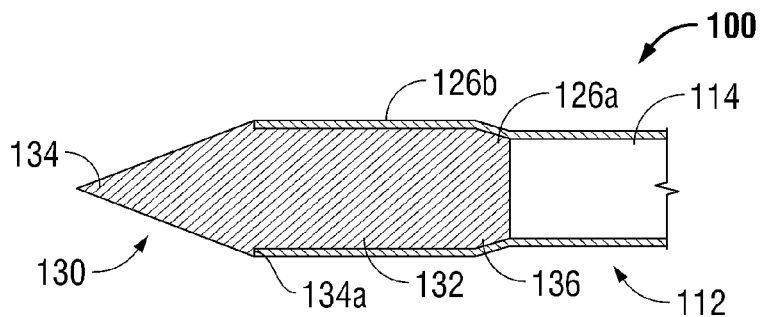
FIG. 5B is a side cross-section view of the plastic tip of the vial access device being inserted into the needle hub assembly shown in FIG. 5A.

In an alternative embodiment shown in FIGS. 5A-5B, a vial access device 100 includes a metal cannula 114 and a plastic tip 130. The plastic tip 130 includes a piercing distal end 134, a tapered proximal end 136, a central portion 132 and channel grooves 138. The distal end 134 also includes a flanged portion 134a. Flanged portion 134a abuts the blunt distal end 126b of the metal cannula 114, thus keeping the plastic tip 130 securely attached to the metal cannula 114, as shown in FIGS. 5A and 5B. Metal cannula 114 has a distal end 126 that comprises a flared portion 126a, which flares outwardly to a large diameter portion 126b. Large diameter portion 126b is dimensioned to receive the plastic tip 130. By providing a large diameter portion 126b at the distal end of cannula 114, a large diameter plastic tip 130 can be supported in the distal end of cannula 114. A large diameter plastic tip 130 is advantageous (over a smaller diameter plastic tip) because the large diameter tip provides greater surface area for larger channel grooves 138. The tapered proximal end 136 of the plastic tip is configured to abut the flared portion 126a of the distal end 126 of metal cannula 114. The central portion 132 of plastic tip 130 is configured to be substantially the same width as large diameter portion 126b of metal cannula 114, thus creating a tight secure fit of plastic tip 130 with the distal end of cannula 114. The plastic insert 130 can be secured to the distal end 126 of the metal cannula 114 by friction, glue, snap-fit, crimping, or using any other suitable connecting technique.

Similarly to plastic tip 30, the plastic tip 130 comprises an external portion 138' and an internal portion 138, which runs along the length of the plastic tip 130. The external channel groove 138' is positioned distally of metal cannula 114 when plastic tip 130 has been securely inserted into the distal end 126 of metal cannula 114, as shown in FIG. 5B. Channel grooves 138' and 138 create a continuous flow path from distal end 134 of tip 130 to the proximal end 136 of the plastic tip 130 through outlet 128 of metal cannula 114 to allow medicinal fluid or any type of fluid to flow into a syringe. As mentioned above, the large diameter portion 126b of metal cannula 114 allows for a large diameter plastic tip 130, which in turn, provides for larger channel grooves 138' and 138. The larger channel grooves 138' and 138 have a greater area for a greater amount of fluid to flow into metal cannula 114. The plastic tip 130 may have more than one channel groove, as shown in FIG. 3C.

Figure 6A:
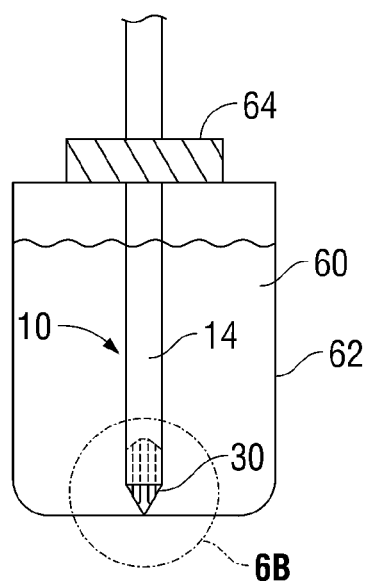
FIG. 6A is a side view of the vial access device of FIG. 1 being inserted into a vial.

In use, the vial access device 10 is connected in fluid communication to the syringe assembly 42. As depicted in FIG. 6A, the user inserts the vial access device 10 into a medical vial 62 by piercing a pierceable septum 64 with plastic tip 30. The vial 62 may contain any necessary medicinal fluid 60 appropriate for a particular medical procedure. The vial access device 10 may be inserted through septum 64 of the vial 62 such that plastic tip 30 engages a bottom portion of vial 62 to retrieve the medicinal fluid 60. The user then pulls the plunger assembly 46 of the syringe 42 and extracts the appropriate amount of fluid 60 necessary for the particular medical procedure.

Figure 6B:
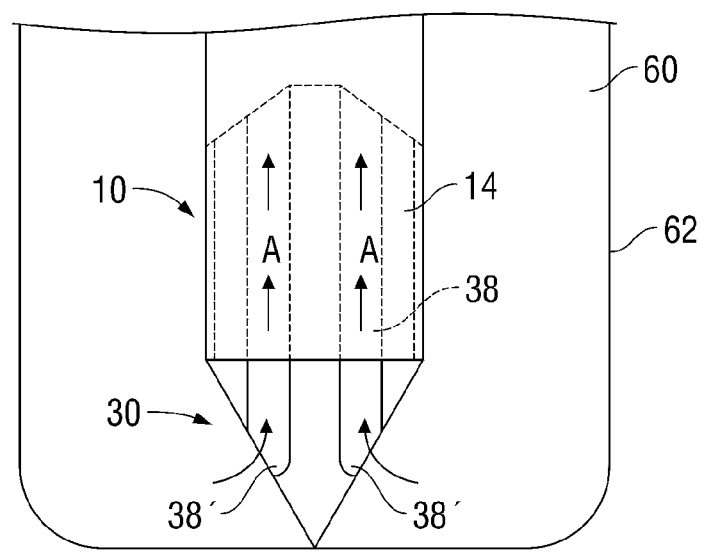
FIG. 6B is a close-up view of the vial access device shown in FIG. 6A.

As shown in more detail in FIG. 6B, the fluid 60 contained in the vial 62 flows along the fluid flow path "A" into the external grooves 38'a-c of the plastic tip 30 and through the internal grooves 38a-c channeling into the metal cannula 14, where it further flows into reservoir 50 of syringe 42 (not shown). Vial access device 10 can now be withdrawn from vial 62.

The user may then remove the needle hub assembly 12 and replace it with a puncturing needle (not shown) for directly injecting the medicinal fluid into a patient. Alternatively, other suitable cannula or needle hub assemblies may be secured to a distal end of the syringe (e.g., oral dose adapter, indwelling catheter, etc.) for delivery of the medicinal fluid from the syringe reservoir to the patient.

Although the illustrative embodiments of the present disclosure have been described herein with reference to the accompanying drawings, it is to be understood that the disclosure is not limited to those precise embodiments, and that various other changes and modifications may be effect therein by one skilled in the art without departing from the scope or spirit of the disclosure.

What is claimed is:

1. A needle assembly comprising:
   a needle hub defining a fluid flow path therethrough;
   a metal cannula adapted to be supported on a distal end of the needle hub, the metal cannula defining a fluid flow path into the distal end of the needle hub, wherein a distal end of the metal cannula includes a first inner diameter portion and a second inner diameter portion interconnected by a tapered portion, the second inner diameter portion being greater in diameter than the first inner diameter portion and being dimensioned to receive a proximal end of a plastic tip; and
   the plastic tip operatively connected to the distal end of the metal cannula, the plastic tip including a distal end having a distal piercing surface, a central portion having an outer diameter which corresponds to the second inner diameter portion of the metal cannula and a tapered proximal end which tapers to a smaller diameter, the tapered proximal end being configured to abut the tapered portion of the metal cannula.

2. The needle assembly according to claim 1, wherein the plastic tip defines at least one channel groove running along at least a portion of the length of the plastic tip, the at least one channel groove being configured to allow fluid to flow into a distal end of the metal cannula.

3. The needle assembly according to claim 1, wherein the distal piercing surface of the plastic tip is configured to pierce a septum of a vial.

4. The needle assembly according to claim 1, wherein the plastic tip is formed from a thermoformable material and the shape of the distal piercing surface is achieved by manufacture using a mold.

5. The needle assembly according to claim 1, wherein the needle hub includes a coupling member for releasably engaging a cooperating member of a syringe.

6. The needle assembly according to claim 1, further comprising:
   a syringe assembly having a plunger assembly and a syringe body, the syringe assembly operably and fluidly connected to the needle hub.

7. The needle assembly according to claim 1, further comprising:
   a syringe assembly including:
   a syringe body defining a fluid reservoir and a fluid outlet;
   a plunger assembly having a plunger rod and a plunger head, the plunger head configured to be slidably received within the fluid reservoir of the syringe body, the plunger head further being configured to deliver fluid from the fluid reservoir to the needle hub.

8. The needle assembly according to claim 7, wherein the needle hub includes a tubular body portion defining the fluid flow path fluidly connected to the metal cannula, a grip portion, and a first coupling member configured to releasably engage a second coupling member of the syringe assembly to releasably secure the needle hub to the syringe assembly.

9. The needle assembly according to claim 8, wherein the first coupling member defines a female luer-type connector, the first coupling member having a plurality of tabs configured to rotatably engage threads of the second coupling member of the syringe assembly.

10. The needle assembly according to claim 9, wherein the second coupling member defines a male luer-type connector.

11. The needle assembly according to claim 1, wherein the distal piercing distal surface defines an arrow-shaped point which is configured to pierce a penetrable member, and the plastic tip defines a central segment in fluid flow communication with a proximal end of the plastic tip.

12. The needle assembly according to claim 1, wherein the plastic tip includes a flanged portion operably positioned to engage the distal end of the metal cannula.

13. The needle assembly according to claim 1, wherein the plastic tip is coupled to the distal end of the metal cannula by a fastening technique selected from the group consisting of gluing, snap-fitting, crimping, press-fitting, and molding.

14. The needle assembly according to claim 2, wherein the at least one channel groove of the plastic tip extends partially within the distal end of metal cannula and defines a continuous flow path into the metal cannula.

15. A needle assembly comprising:
   a needle hub defining a fluid flow path therethrough;
   a metal cannula adapted to be supported on a distal end of the needle hub, the metal cannula defining a fluid flow path into the distal end of the needle hub, wherein a distal end of the metal cannula includes a first inner diameter portion and a second inner diameter portion interconnected by a tapered portion, the second inner diameter portion being greater in diameter than the first inner diameter portion and being dimensioned to receive a proximal end of a plastic tip; and
   the plastic tip operatively connected to the distal end of the metal cannula, the plastic tip including a distal end having a distal piercing surface and defining a fluid flow path into the distal end of the metal cannula, and a central portion having an outer diameter which corresponds to the second inner diameter portion of the metal cannula and a tapered proximal end which tapers to a smaller diameter, the tapered proximal end being configured to abut the tapered portion of the metal cannula, wherein the plastic tip defines at least one channel groove running along at least a portion of the length of the plastic tip, the at least one channel groove being configured to allow fluid to flow into a distal end of the metal cannula, the distal piercing surface of the plastic tip being configured to pierce a septum of a vial, and wherein the plastic tip is formed from a thermoformable material and the shape of the distal piercing surface is achieved by manufacture using a mold.

16. The needle assembly according to claim 15, wherein the at least one channel groove of the plastic tip extends partially within the distal end of metal cannula and defines a continuous flow path into the metal cannula.

* * * * *